United States Patent [19]

Braid

[11] Patent Number: 4,466,925

[45] Date of Patent: Aug. 21, 1984

[54] METHOD FOR THE PREPARATION OF TRANSITION METAL COMPLEXES

[75] Inventor: Milton Braid, Haddonfield, N.J.

[73] Assignee: Mobil Oil Corporation, New York, N.Y.

[21] Appl. No.: 366,952

[22] Filed: Apr. 9, 1982

[51] Int. Cl.$^3$ .............................................. C07F 15/04
[52] U.S. Cl. ............................ 260/439 R; 260/429 R
[58] Field of Search ........................ 260/439 R, 429 R

[56]  References Cited

U.S. PATENT DOCUMENTS

| | | | |
|---|---|---|---|
| 2,971,941 | 2/1961 | Fuchsman et al. | 260/439 R X |
| 4,119,548 | 10/1978 | Braid | 260/439 R X |
| 4,151,100 | 4/1979 | Braid | 260/439 R X |
| 4,198,303 | 4/1980 | Braid | 260/439 R X |

Primary Examiner—Helen M. S. Sneed
Attorney, Agent, or Firm—Alexander J. McKillop; Michael G. Gilman; Howard M. Flournoy

[57] ABSTRACT

A method for the preparation of complexes of transition metal 2,2'-thiobis(alkylphenolates) with hydroxyorganic ligands which comprises the direct reaction of the thiobis(alkylphenol), with an alkali metal carbonate and a transition metal salt in a hydroxyorganic reactant-solvent. The initial hydroxyorganic ligand can be partially or totally replaced without isolation. The complexes are employed as stabilizers for lubricants, plastics and fuels.

6 Claims, No Drawings

METHOD FOR THE PREPARATION OF TRANSITION METAL COMPLEXES

BACKGROUND OF THE INVENTION

1. Field of the Invention

The present invention relates to a simplified direct method for the preparation of transition metal complexes of 2,2'-thiobis(alkylphenolates) with hydroxyorganic ligands wherein the initial hydroxyorganic ligand is employed both as a reactant and as a solvent. These transition metal complexes such as, for example, nickel (II) thiobis-(alkylphenolates) when complexed with hydroxyl-substituted ligands such as alcohols and phenols may be added to organic compositions, normally subject to oxydative degredation such as lubricants and plastics, to impart anti-oxidant and ultra-violet stabilization thereto.

2. Brief Description of the Prior Art

The production of lubricant compositions, for example, lubricating oils produced by hydrocracking provides a relatively high viscosity index oil and permits the use of base stocks that would be unsuitable for other purposes. On the other hand, however, hydrocracked lubricating oils tend toward poor stability against ultraviolet light degradation, rapidly forming suspended and/or precipitated insoluble material on exposure to ultraviolet light, such as sunlight, or other sources of actinic radiation. Additionally lubricants may be subjected to high temperatures which tend as mentioned heretofore to catalyze oxidative degradation.

Commercially available ultraviolet stabilizers are listed by class and function and identified as to structure in the Kirk-Othmer Encyclopedia in "Encyclopedia of Chemical Technology"; Second Edition, Vol. 21, pp. 115–122. U.S. Pat. No. 3,832,304 dicloses the use of aromatic azo compounds for stabilizing hydrocracked oils. U.S. Pat. Nos. 2,703,786; 2,716,090 and 3,210,277 disclose the use of polyvalent metal, e.g., Ni salts of thiobis(alkylphenols) as oxidation inhibitors and plasticizing agents. Nickel thiobis-(4-t-octylphenolate) is disclosed in U.S. Pat. No. 2,971,940 as a stabilizer for plastics and complexes thereof with amines, e.g., n-butylamine are disclosed in U.S. Pat. No. 3,215,717 as plastic stabilizers.

Additionally, in the prior art, transition metal phenolate complexes of 2,2'-thiobis(alkylphenols) which have hydroxyorganic ligands have been employed as stabilizers for a wide variety of lubricants, greases, and plastics. For example, nickel complexes have been found useful in stabilizing plastics such as polyolefins against the deteriorative action of ultraviolet light. When employed with lubricants, such additives also have a stabilizing effect in that they prolong the useful life of a lubricant by increasing its resistance to oxidation.

In the past, methods have been disclosed in the prior art for the preparation of such transition metal phenolates of 2,2'-thiobis(alkylphenol) in a first step to produce the transition metal complex of the 2,2'-thiobis(alkylphenol). The resultant metal complex is subsequently reacted with the desired hydroxyorganic ligand to form the final transition metal complex. Such prior art includes U.S. Pat. Nos. 3,313,770, and 4,198,303, the disclosures of which are incorporated herein by reference wherein it is taught that to form the desired transition metal complex a 2,2'-thiobis(alkylphenol) is reacted with a nickel compound such as nickel nitrate to eventually form the nickel 2,2'-thio-bis(alkylphenol) which is then subsequently reacted in a separate step with the hydroxyorganic ligand to form the desired transition metal complex.

SUMMARY OF THE INVENTION

In accordance with the present invention, it has been found that 2,2'-thiobis(alkylphenols) can, as contrasted with the aforedescribed prior art, be readily and far more simply converted to transition metal complexes containing simple hydroxy ligands. Further, the initial hydroxyorganic ligand then, if desired, may be displaced totally or partially by a different ligand by one additional step. Thus, a transition metal complex of 2,2'-thiobis(alkylphenolate) with a hydroxyorganic ligand may be prepared in accordance with the present invention by reacting in one mixture, 2,2'-thiobis(alkylphenol), anhydrous potassium carbonate or other suitable base, and a suitable transition metal salt and a hydroxy- organic solvent-reactant which is the intended ligand. Thus, 2,2'-thiobis-(4-tert-octylphenol), potassium carbonate, and nickel chloride in 2-propanol produces directly in a short reaction time a nickel 2,2'-thiobis-(4-tert-octylphenolate).2-propanol complex. Optionally, this complex, without isolation from the reaction mixture, by reaction with a stoichiometric equivalent of a different hydroxyorganic ligand, produces upon removal of all 2-propanol a new corresponding complex of the second hydroxyorganic ligand. Partial replacement of the initial ligand produces mixed hydroxyorganic complexes.

Any suitable hydroxy-substituted ligand may be used in the method of the present invention to form the coordination complex. A non-exhaustive list includes methanol, ethanol, propanol, 2-propanol, n-butanol, isobutyl alcohol, benzyl alcohol, 3,5-di-tertiary-butyl-4-hydroxybenzyl alcohol, phenol, 1,4-butanediol, 1,6-hexamethylenediol, 1,8-octamethylenediol, 1,4-cyclohexanedimethanol and the like.

Particularly preferred are alcohols having from 1 to about 4 carbon atoms such as methanol, ethanol, 2-propanol, propanol and butanols; and phenol.

The 2,2'-thiobis(alkylphenols), which are employed in accordance with the method of the present invention, are well known compounds, and may readily be prepared by known means such as reaction of a p-alkylphenol with $SCl_2$. Examples of 4-alkylphenol sulfides which may be employed in the method of the present invention include the following:

2,2'-thiobis(p-octylphenol)sulfide,
2,2'-thiobis(p-butylphenol)sulfide,
2,2'-thiobis(p-cyclohexylphenol)sulfide,
2,2'-thiobis(p-nonylphenol)sulfide,
2,2'-thiobis(p-ethylphenol)sulfide,
2,2'-thiobis(p-amyphenol)sulfide,
2,2'-thiobis(p-t-dodecylphenol)sulfide and
2,2'-thiobis(p-octadecylphenol)sulfide.

The organosulfur-containing hyroxy-substituted nickel complexes produced in accordance with the method of the present invention may be represented by the following structural formula:

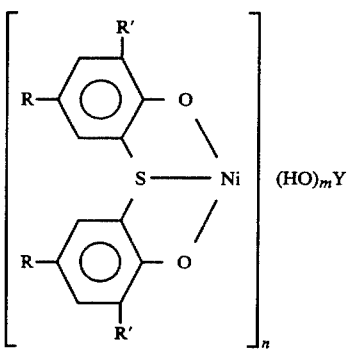

where R is either hydrogen or an alkyl group having from 1 to about 30 carbon atoms, R' is hydrogen or an alkyl group containing from 1-8 carbon atoms, in any isomeric configuration except those in which a carbon atom bonded to a ring carbon atom is in turn bonded to more than two other carbon atoms, and Y is an alkyl, alkylene, aralkyl, alkaryl or alkylene aryl group having from 1 to about 40 carbon atoms, n is from 1 to 4 and m is from 1 to 6 with the proviso that m is never less than n.

The organo-sulfur containing hydroxy-substituted nickel complexes produced in accordance with the method of the present invention may be effectively employed in any amount which is sufficient for imparting to the organic medium, e.g., lubricant, the desired degree of protection against oxidative degradation. In many instances, the complex is effectively employed in an amount from about 0.01 to about 5% by weight, and preferably in an amount from about 0.1 to about 2% by weight, of the total weight of the lubricant composition. As hereinbefore indicated, the novel organic sulfur-containing hydroxy-substituted ligand nickel complexes may be incorporated in any organic media normally subject to oxidative degradation, for example lubricating media which can include oils of lubricating viscosity or greases prepared therefrom in which any of the aforementioned oils or fluids may be employed as vehicles. In general, synthetic oils can also be effectively protected against oxidative and UV degradation. They may also be employed in combination with mineral oils, or as grease vehicles. Typical synthetic vehicles includes polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis-(p-phenoxyphenyl)ether, phenoxy phenylether, etc. Generally speaking it is more particularly concerned with areas of lubricating viscosity hydrocarbon fuels and fuel oils which may be mineral oils or fractions thereof or synthetic oils as described hereinabove. With respect to synthetic base stock, ester base stock is preferred.

A non-exhaustive list of suitable arylamine co-antioxidants useful herein are preferably selected from the group consisting of the following: N-phenyl-1-naphthylamine; N-(4'-t-octylphenyl)-1-naphthylamine; N-phenyl-2-naphthylamine, 4,4'-thiobis(n-phenyl-1-naphthylamine); 1,1'-thiobis (N-phenyl-2-naphthylamine); diphenylamine; 4,4'-di-t-octyldiphenylamine; dinaphthylamine; 4-decoxydiphenylamine; phenothiazine. Especially preferred are phenyl naphthylamines such as N-phenyl-1-naphthylamine, N-(4-t-octylphenyl)-1-naphthylamine and N-phenyl-2-naphthylamine. However, it is understood that this is a non-limiting list and any arylamine appropriate in view of those disclosed above may be used.

Any suitable hinered phenolic compound may be used herein as a co-antioxidant. Preferred are those selected form the following non-exhaustive list: 2,6-di-t-butyl-p-cresol; 4,4'-methylenebis-(2-6-di-t-butyl-m-cresol); 4,4'-butylidenebis-(6-t-butyl-m-cresol); 4,4'-methylenebis-(2,6-di-t-butylphenol); 2,6-di-t-butylphenol, and 4,4'-butylidenebis-2,6-di-t-butylphenol) 2,4,6-tri-t-butylphenol. Especially preferred is 4,4'-methylenebis-(2,6-di-t-butylphenol).

Generally, the weight ratio of nickel complex to arylamine and/or hindered phenol is from about 0.01-5.0 to 1.

The following examples are intended to illustrate specific embodiments of the method of the present invention, and hence are not meant to be construed in a limiting sense.

DESCRIPTION OF SPECIFIC EXAMPLES

EXAMPLE 1

Preparation of 2-propanol complex of nickel 2,2'-thiobis-(4-t-octylphenol)

To a solution of 4-(1,1,3,3-tetramethylbutyl) phenol sulfide, 2,2'-thiobis-(4-t-octylphenol), 44.3 g, in 2-propanol, 150 g, there was added while stirring at 30° C., potassium carbonate, 27.6 g, and the reaction mixture temperature was raised to 60° C. To the resulting solution-suspension there was added nickel chloride hexahydrate, 23.8 g, and the temperature of the reaction mixture was then raised to 80° C. After 3 hr. of refluxing, the 2-propanol was stripped and the green solids residue was extracted with n-hexane. Removal of n-hexane from the extract left the 2-propanol complex of nickel 2,2'-thiobis-(4-t-octylphenolate) as a green solid melting above 300° C. The infrared spectrum of this green solid product matched that of the same complex prepared by treating 2,2'-thiobis-(4-t-octylphenolphenolate) with 2-propanol as in Example 4 of U.S. Pat. No. 4,198,303, the disclosure of which has been incorporated herein by reference.

EXAMPLE 2

Preparation of nickel 2,2'-thiobis-(4-t-octylphenol-phenolate) via the 2-propanol complex of nickel 2,2'-thiobis-(4-t-octylphenolate) formed in situ.

To a solution of 4-(1,1,2,2-tetramethylbutyl) phenol sulfide, 2,2'-thiobis-(4-t-octylphenol), 44.3 g., in 2-propanol, 150 g., stirred at 30° C. there was added potassium carbonate, 13.8 g., and the temperature of the resulting solution-suspension was raised to 60° C. Nickel chloride hexahydrate, 23.8 g., was added and the reaction mixture was refluxed at 80° C. for a total of 3 hrs. During this reaction period the 2-propanol complex of nickel 2,2'-thiobis-(4-t-octylphenolate) separated as a green solid (m.p. greater than 300° C.) heterogeneous phase. Solvent 2-propanol was distilled from the reaction mixture and during this distillation 2-propanol was also displaced from its nickel thiobis alkylphenolate complex by 2,2'-thiobis-(4-t-octylphenol). Extraction of the green solids distillation residue with n-hexane and removal of the n-hexane from the extract left nickel 2,2'-thiobis-(4-t-octylphenol-phenolate) as a green solid mp 142°–146° C. with an infrared spectrum matching that of the same complex prepared via reaction of 2,2'-thiobis-(4-t-octylphenol) with nickel acetate in xylene.

EXAMPLE 3

Preparation of Complex of 2,2' Thiobis-and 2,2'-Polythiobis-(4-t-octylphenol) Mixture To a solution of the mixture of 2,2'-thiobis(4-t-octylphenol 2,2'-dithiobis-(4-t-octylphenol) and 2,2'-polythiobis-(4-t-octylphenol) prepared by reaction of 4-t-octylphenol with sulfur monochloride at 127° C., 45.1 g., in 2-propanol, 300 ml, heated to just below reflux temperature there was added while stirring potassium carbonate, 18 g. To the resulting solution-suspension reaction mixture there was then added in portions during ten minutes nickel chloride, 45.8 g., and the mixture was stirred for 3 hrs. and filtered. Removal of solvent and volatiles left the oil soluble nickel-and 2 propanol-containing complex as a greenish-brown solid containing 65.17% of carbon, 7.70% of hydrogen, 14% of sulfur and 4.26% of nickel.

EXAMPLE 4

Preparation of Nickel Complex of Oligomeric 2,2'-Thiobis-and 2,2'-Polythiobis-(4-t-amylphenol)

To a solution of the mixture of oligomeric 2,2'-triobis-(4-t-amylphenol), 2,2'-dithiobis-(4-t-amylphenol) and 2,2'-polythiobis-(4-t-amylphenol) commercial rubber vulcanizing agent (identified as Vultic 186 by the Pennwalt Corp.) in ethanol, 400 ml, there was added potassium carbonate, 10 g., and then nickel chloride, 23.7 g., all at reflux temperature. The resulting reaction mixture was heated at reflux and stirred for several hours. Solvent was removed by rotary film evaporation leaving a yellow hard solids mixture. The solids were extracted with benzene. Benzene was stripped from the extract and the residue was re-extracted with cyclohexane. Removal of cyclohexane left the product complex as a mustard colored yellow solid m.p. 96°–100° C., containing 53.06% carbon 6.46% hydrogen, and 5.73% of nickel.

The additives prepared in accordance with the preceeding examples were incorporated into a base oil for catalytic oxidation testing. The base oil employed was a refined solvent mineral oil characterized by a viscosity of 4.95Cs at 210° F.

A sample of the base lubricant is placed in an oven at a desired temperature. Present in the sample are the following metals either known to catalyze organic oxidation or commonly used materials of construction.
  a. 15.6 sq. in. of sand-blasted iron wire,
  b. 0.78 sq. in. of polished copper wire,
  c. 0.87 sq. in. of polished aluminum wire, and
  d. 0.167 sq. in. of polished lead surface.

Dry air is passed through the sample at a rate of about 5 liters per hour.

TABLE 1

| CATALYTIC OXIDATION TEST 325° F., 40 HR. MINERAL OIL BASE STOCK | | | |
|---|---|---|---|
| Additive | Conc, Wt. % | Delta NN | Delta KV % |
| None | — | 17 | 334 |
| 1 | 1 | 5.5 | 77 |
| 2 | 1 | 2.4 | 26 |
| 3 | 1 | 2.6 | 28 |
| 4 | Less than 1 | 6.4 | 59 |

The data set forth in the preceeding Table clearly demonstrates the utility of the complexes formed in accordance with the method of the present invention.

What is claimed is:

1. In a method for the preparation of complexes of transition metal 2,2'-thiobis(alkylphenolates) with hydroxy-organic ligands, the improvement which comprises the direct reaction of said thiobis(alkylphenol) with an alkali metal carbonate and a transition metal salt in a hydroxyorganic reactant-solvent in a weight ratio of hydroxyorganic reactant-solvent to transition metal salt to alkali metal carbonate of from about 1.5–1:1 to about 40–2.5:1 at reflux temperatures.

2. The method in accordance with claim 1 wherein said complex which is produced has the following general structure

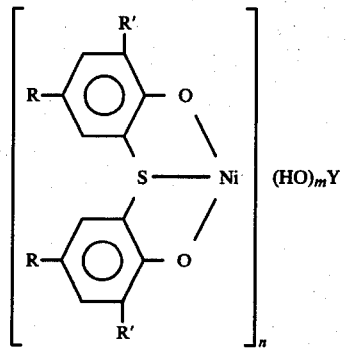

where R is either hydrogen or an alkyl group having from 1 to about 30 carbon atoms, R' is hydrogen or an alkyl group containing from 1–8 carbon atoms in any isomeric configuration except those in which a carbon atom bonded to a ring carbon atom is in turn bonded to more than two other carbon atoms, Y is alkyl, alkylene, aralkyl, alkaryl or alkylene aryl of from 1 to about 40 carbon atoms and n is from 1 to 4 and m is from 1 to 6 with the proviso that m is never less than n.

3. A method in accordance with claim 1 wherein said metal carbonate is potassium carbonate.

4. A method in accordance with claim 1 wherein said transition metal salt is a nickel salt.

5. A method in accordance with claim 1 wherein said transition metal salt is nickel chloride.

6. A method in accordance with claim 1 wherein Y is a ligand such that Y (OH) is methanol, ethanol, n-propanol, i-propanol, n-butanol, i-butanol, benzyl alcohol, 3,5-ditertiary-butyl-1,4-hydroxybenzyl alcohol, phenol, 1,4-butanediol, 1,6-hexamethylenediol, 1,8-octamethylenediol, or 1,4-cyclohexanedimethanol.

* * * * *

UNITED STATES PATENT AND TRADEMARK OFFICE
CERTIFICATE OF CORRECTION

PATENT NO. : 4,466,925
DATED : August 21, 1984
INVENTOR(S) : MILTON BRAID

It is certified that error appears in the above-identified patent and that said Letters Patent are hereby corrected as shown below:

Column 2, line 61, "(p-amyphenol) should be --(p-amylphenol)--.

Column 3, line 68," (n-phenyl" should be--(N-phenyl--.

Claim 1, lines 22 and 23, "1.5-1.1" should be --6:1:1-- and "40-2.5:1" should be 32:2.5:1--.

Signed and Sealed this

Twenty-sixth Day of March 1985

[SEAL]

Attest:

DONALD J. QUIGG

Attesting Officer

Acting Commissioner of Patents and Trademarks